United States Patent [19]

Fernandez et al.

[11] Patent Number: 5,045,634
[45] Date of Patent: Sep. 3, 1991

[54] FLUORINATION OF HALOOLEFINS

[75] Inventors: Richard E. Fernandez, Bear; William H. Gumprecht; Kaplan, Ralph B., both of Wilmington, all of Del.

[73] Assignee: E. I. Du Pont de Nemours and Company, Wilmington, Del.

[21] Appl. No.: 545,248

[22] Filed: Jun. 28, 1990

[51] Int. Cl.$^5$ .................... C07C 17/20; C07C 19/08; C07C 21/18
[52] U.S. Cl. .................... 570/170; 570/175; 570/166; 570/153; 570/160
[58] Field of Search ............... 570/170, 235, 153, 160, 570/166, 175

[56] References Cited

U.S. PATENT DOCUMENTS

| | | | |
|---|---|---|---|
| 2,842,603 | 7/1958 | Miller | 570/160 |
| 3,287,425 | 11/1966 | Maynard | 570/160 |
| 3,872,174 | 3/1975 | Bellis | 570/235 |
| 4,158,675 | 6/1979 | Potter | 260/653.7 |
| 4,311,863 | 1/1982 | Gumprecht | 570/170 |
| 4,734,526 | 3/1988 | Albert et al. | 564/282 |
| 4,780,559 | 10/1988 | Brown et al. | 558/425 |

FOREIGN PATENT DOCUMENTS 941144 11/1963 United Kingdom .

*Primary Examiner*—Alan Siegel

[57] ABSTRACT

A process for fluorination by contacting a haloolefin with molten alkali metal acid fluoride to provide a fluorinated saturated or unsaturated hydrocarbon having at least one more fluorine than the starting haloolefin.

6 Claims, No Drawings

5,045,634

FLUORINATION OF HALOOLEFINS

FIELD OF THE INVENTION

This invention relates to the fluorination of a halocarbon to another halocarbon having at least one additional fluorine-substitution than the original halocarbon. More particularly, the invention relates to the conversion of an unsaturated halocarbon, i.e., a haloolefin, having at least one chlorine or bromine or fluorine substitution to a saturated or unsaturated halocarbon having at least one fluorine adding onto or replacing the at least one halogen substitution. Of greatest interest is the invented process for improving the conversion of haloolefins such as $CHCl=CCl_2$ and $CCl_2=CCl_2$, to such fluorinated products as 1,1,1,-trifluorochloroethane, $CF_3CH_2Cl$ (HCFC-133a); 1,1,1,2-tetrafluoroethane, $CF_3CH_2F$ (HFC-134a); 2,2-dichloro-1,1,1-trifluoroethane, $CF_3CHCl_2$ (HCFC-123); 1,1,1,2-tetrafluoro-2-chloroethane; $CF_3CHClF$ (HCFC-124); and pentafluoroethane, $CF_3CHF_2$ (HFC-125); and, optionally, recovering the resulting metal chloride as the metal fluoride for recycling into the conversion process.

BACKGROUND OF THE INVENTION

The hydrogen-containing fluorinated hydrocarbons, having low ozone depletion potentials, are candidates to replace certain commercial perhalocarbons suspected of contributing to the destruction of stratospheric ozone. One route to hydrogen-containing fluorinated materials involves addition of HF to an appropriate haloolefin, followed, if necessary to achieve a desired fluorine content, by halogen exchange fluorination of the HF adduct. Although various such reaction schemes are known, none is entirely satisfactory from a commercial standpoint. With few exceptions, a catalyst is required for practical results. Even so, many of the catalysts are inherently limited as to the degree of fluorination they can provide. The more effective catalysts, generally transition metal compounds, are expensive, often requiring specialized methods for their preparation and maintenance.

Furthermore, whatever catalyst is used, rather large excesses of HF over the stoichometric amounts are usually required, particularly to attain multiple halogen exchange fluorinations of the initially formed HF adduct. The burden of processing the excess corrosive HF adds significantly to the investment in equipment as well as the operating costs of the process.

PRIOR ART

U.S. Pat. No. 4,734,526 Albert et al. discloses the reaction of quaternary ammonium acid fluorides with acetylenic compounds to form fluorinated olefinic derivatives. The patentees state that the reaction is specific to the acetylenes and that further reaction of the acid fluoride with the haloolefinic product of the HF additive reaction does not occur.

U.S. Pat. No. 4,780,559 Brown et al. discloses the use of phosphonium acid fluorides as halogen exchange agents. The patentees states that the alkali metal acid fluorides are ineffective for this purpose.

Halogen exchange processes are also known wherein haloolefins are formed as troublesome impurities. One such process comprises the vapor phase reaction of $CF_3CH_2Cl$(HCFC-133a) with HF to produce $CF_3CH_2F$(HCFC-134a), a potential replacement for the commercial refrigerant $CCl_2F_2$(CFC-12). Accompanying the tetrafluoroethane product is a toxic haloolefin, $CHCl=CF_2$(CFC-1122), whose boiling point is close enough to that of the tetrafluoroethane to make it difficult to remove by distillation. Here, too, the processes disclosed for removing this haloolefinic material from the desired $CF_3CH_2F$ leave much to be desired.

It is an object of this invention to provide a process for the addition of HF to haloolefins which overcomes or minimizes the disadvantages of the prior art. The process of this invention will also provide in situ fluorination of the HF addition product and can produce one or more hydrogen-containing saturated fluorocarbons having at least two more fluorine substituents than the initially employed haloolefin.

Another object is to provide a process that can produce one or more fluorinated haloolefins having at least one or more additional fluorine substituents than the starting haloolefin; and a process that is suitable for removing haioolefinic impurities from a saturated fluorocarbon reaction product.

A further object is to provide a process wherein the spent HF addition and/or in situ halogen exchange agent can be regenerated by relatively simple means.

SUMMARY OF THE INVENTION

The objects are accomplished by a process for preparing fluorinated hydrocarbons comprising:

(1) contacting a haloolefin having at least one halogen substituent attached to an unsaturated carbon atom with an anhydrous, substantially molten alkali metal acid fluoride composition to form a reaction mixture;

(2) maintaining the reaction mixture under agitation at a temperature and pressure for a time sufficient to form at least one saturated or unsaturated hydrocarbon having at least one more fluorine substituent than said haloolefin; and (3) recovering said saturated and/or unsaturated hydrocarbon from the reaction mixture.

A preferred embodiment of the process involves maintaining the reaction mixture in step (2) at the temperature and pressure for a time sufficient to form at least one fluorinated saturated hydrocarbon having at least 2 more fluorine substituents than the haloolefin reactant.

DETAILED DESCRIPTION OF THE INVENTION

In general, the invented process is conducted by intimately contacting or by vigorously agitating, batchwise or continuously, the haloolefin, as previously defined, with an alkali metal acid fluoride composition at an effective temperature and pressure for a time sufficient to result in the formation of at least one fluorinated hydrocarbon having at least one more fluorine in the molecule than the starting haloolefin, and separating the fluorinated reaction product from the residual, at least partially spent (i.e., at least partially depleted of HF content) alkali metal composition.

The process enables the conversion of a variety of open chain and cyclic haloolefins to saturated fluorine-containing compounds by the addition of HF across the double bond thereof. The process is also capable of converting the initially formed HF addition product to more highly fluorinated derivatives thereof via halogen exchange reaction with the alkali metal acid fluoride composition. In other words, the alkali metal acid fluoride can serve both as HF addition reagent and as halogen exchange agent in situ in the initially formed reaction mixture.

The invented process enables one to convert unfluorinated haloolefins, such as triclene ($CHCl=CCl_2$) and perclene ($CCl_2=CCl_2$) to such highly fluorinated and desirable hydrogen-containing saturated products as 1,1,1-trifluorochloroethane ($CF_3CH_2Cl$), 1,1,1,2-tetrafluoroethane ($CF_3CH_2F$), 2,2-dichloro-1,1,1-trifluoroethane ($CF_3CHCl_2$), 1,1,1,2-tetrafluoro-2-chloroethane ($CF_3CHClF$) and pentafluoroethane ($CF_3CHF_2$), in a single step, under relatively moderate conditions.

The process can also yield haloolefins having a higher fluorine content than the starting haloolefin, which products can be treated further in accordance with the invention to produce still more highly fluorinated saturated hydrocarbons.

An important advantage of the process is that it requires less HF per mole of fluorinated product produced than heretofore required, whether through HF addition or halogen exchange. Also, adverse corrosive effects associated with the use of high proportions of HF, as well as the need for high pressure equipment to contain the excess volatile HF component, are minimized. Moreover, since the organic reaction product mixture contains little or no HF, its resolution into its constituents is simplified. In general, the process of the invention is conducted by contacting, batchwise or continuously, a substantially anhydrous haloolefin as defined, in gaseous or liquid form, neat or as a minor component of a saturated product stream, with a substantially anhydrous alkali metal acid fluoride, as defined, in substantially molten or other liquid form. The resulting mixture of reactants is held at the desired temperature and pressure as needed until reaction occurs and there is produced at least one fluorinated saturated compound having at least one more fluorine substituent than the starting haloolefin.

This is further illustrated below with $CCl_2=CCl_2$(CC-1110), a readily available and important starting material in the industry (equation 1).

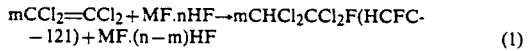

$$mCCl_2=CCl_2 + MF.nHF \rightarrow mCHCl_2CCl_2F(HCFC-121) + MF.(n-m)HF \quad (1)$$

where M is an alkali metal, n is a number of at least about 1, and m is greater than zero and preferably equal to or less than n. Depending upon the value of (n−m) in the residual alkali metal compound and the temperature, further reaction can occur, via halogen exchange between the initially formed saturated HF addition product and the alkali metal compound to produce a more highly fluorinated saturated product (equation 2).

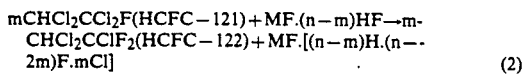

$$mCHCl_2CCl_2F(HCFC-121) + MF.(n-m)HF \rightarrow mCHCl_2CClF_2(HCFC-122) + MF.[(n-m)H.(n-2m)F.mCl] \quad (2)$$

In fact, reaction can proceed further to produce $CHCl_2CF_3$(HFC-123) $CHClFCF_3$(HCFC-124) and $CHF_2CF_3$(HFC-125), all via halogen exchange, depending upon the value of "n" in the alkali metal acid fluoride and its molar proportion relative to that (m) of the organic starting material. The value of (n−m) can be maintained sufficiently high for halogen exchange by adding anhydrous HF, intermittently or continuously, during the course of the reaction. Further, one or more of the saturated products may undergo dehydrohalogenation, evidently via reaction with residual alkali metal fluoride resulting for example, by dissociation of MF·HF into MF and HF, with formation of one or more fluorinated olefins having at least one or more fluorines in the molecule than the starting haloolefin (equation 3).

$$CHCl_2CCl_2F + MF \rightarrow CCl_2=CClF(CFC-1111) + MF.HCl \quad (3)$$

Small amounts of other fluorinated olefins may also be formed, e.g. $CClF=CHCl$, possibly arising through loss of $Cl_2$ from the corresponding chlorofluoroethane. The fluorinated reaction products can be recovered from the reaction mixture by any of the means known to the art, preferably by distillation from the essentially nonvolatile alkali metal composition. The unsaturated components, including unreacted starting material, can be recycled for further reaction with alkali metal acid fluoride to produce more highly saturated products. Alternatively, the fluorinated saturated and unsaturated products of the invention process can be employed as intermediates for the preparation of still other derivatives by processes known to the art.

Thus, it is apparent that the process of this invention is capable of producing a wide range of useful hydrogen-containing fluorinated products, including those used as refrigerants, propellants, sterilants, blowing agents, solvents, fire extinguishing and heat transfer media, as well as chemical intermediates. Another feature of the invention is that spent alkali metal acid fluoride, i.e., the product of equation (1) above, can be regenerated for reuse in the process by treatment in situ or separately with anhydrous HF (equation 4).

$$MF.(n-m)HF + mHF \rightarrow MF.nHF \quad (4)$$

It is also apparent that where the alkali metal composition to be regenerated also contains chloride ion, resulting from halogen exchange between the HF addition product and the spent alkali metal acid fluoride of equation (1), as illustrated in equation (2) above, it can be substantially restored to its initial acid fluoride state by further treatment with HF (equation 5).

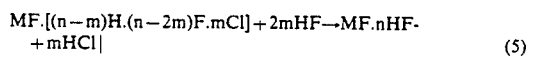

$$MF.[(n-m)H.(n-2m)F.mCl] + 2mHF \rightarrow MF.nHF + mHCl\uparrow \quad (5)$$

The HCl by-product is removable by distillation. Generally, excess HF is employed to ensure such removal.

The alkali metal acid fluorides are well-known compositions and can be represented as MF.nHF, where M stands for at least one alkali metal and n is a number of at least 1, preferably greater than 1.

The alkali metal is preferably potassium (K), rubidium (Rb) or cesium (Cs) more preferably Cs and/or Rb and most preferably predominantly Cs. Any of the other alkali metals and/or other compatible metals (alkaline earth or aluminum) may be present in minor accounts. Preferably, the alkali metal acid fluoride is employed in the substantially anhydrous molten state. In general, the higher the value of n (in MF.nHF) and the greater the atomic weight of the alkali metal, the lower is the melting point of the alkali metal acid fluoride. Preferably, the acid fluoride will be so constituted as to be substantially molten below about 250° C. and, more preferably, below about 225° C. The acid fluoride composition may also contain alkali metal halides other than the fluorides. These can vary widely as to the metal, the halide and their amounts provided that the resulting alkali metal composition contains sufficient HF so that the composition MX.nHF, where X is a mixture of a major proportion of fluoride and a minor amount of halide other than fluoride, and n is at least 1 as defined above, and the composition is substantially molten below about 250° C.

By substantially molten is meant that the alkali metal acid fluoride composition in the molten state may contain insoluble matter, such as metal salt by-products of halogen exchange reactions, so long as the liquid phase contains alkali metal acid fluoride and is stirrable. The quantity of the alkali metal acid fluoride may vary widely depending on its molar proportion, and the value of "n" in MF.nHF and the result desired, that is, to what extent halogen exchange fluorination of the primary HF addition product of equation (1) is desired as illustrated in equation (3). Generally, at least about a single molar proportion of MF.nHF will be employed, preferably an excess, with not more than about 10 molar proportions being normally needed for the purposes of the invention. As stated previously, the value of "n" can be maintained at an effective level by the addition of HF as needed during the course of the reaction.

Progress of the reaction can be followed by following the changes in the organic component of the reaction mixture. In general, high values of "n" favor HF addition; low values favor halogen exchange of the saturated HF addition product provided the product contains a replaceable halogen, i.e., other than fluoride. If desired, once the HF addition product is formed to the desired extent, alkali metal fluoride can be added to the reaction mixture to lower the overall value of "n" in the mixture, even to a level below 1. During the halogen exchange phase of the overall reaction, the value of "n" can be allowed to decrease to as low as 0.5, preferably not below about 0.8, provided the reaction mixture remains molten to the extent of being stirrable.

The haloolefin, which can be acyclic or cyclic, can vary widely. The haloolefin will normally contain 2 to 6 carbon atoms, preferably 2 to 3, more preferably 2 carbon atoms, in the molecule. The halogens are preferably chlorine and/or fluorine substituents because of their greater availability and economic importance. The presence of one or more non-fluorine halogen substituents are required, if in situ halogen exchange fluorination is to be effected.

Representative and preferred haloolefins are represented by the formula, $RCX=CX_2$, wherein R is X or $CY_3$; X is H, Cl or F and at least one is Cl or F; and Y is H, Cl or F. Typical haloethylenes, halopropylenes and other haloolefins that can be fluorinated in accordance with the process of the invention are tabulated below along with some of the corresponding hydrogen-containing fluorinated saturated products that may be prepared therefrom by HF addition followed by halogen exchange reaction of the HF adduct with the residual alkali metal acid fluoride.

| Haloolefins | Saturated Fluorinated Products |
| --- | --- |
| $CH_2=CHCl$ | $CH_3CHClF$, $CH_3CHF_2$ |
| $CH_2=CHF$ | $CH_3CHF_2$ |
| $CH_2=CF_2$ | $CH_3CHF_3$ |
| $CH_2=CClF$ | $CH_3CClF_2$, $CH_3CF_3$ |
| $CH_2=CCl_2$ | $CH_3CCl_2F$, $CH_3CClF_2$, $CH_3CF_3$ |
| $CHF=CF_2$ | $CH_2FCF_3$ |
| $CHCl=CF_2$ | $CHClFCF_3$ |
| $CCl_2=CCl_2$ | $CHCl_2CCl_2F$, $CHCl_2CClF_2$, $CHCl_2CF_3$, $CHClFCF_3$, $CHF_2CF_3$ |
| $CClF=CCl_2$ | $CHClFCCl_2F$, $CHClFCClF_2$, $CHClFCF_3$, $CHF_2CF_3$ |
| $CCl_2=CF_2$ | $CHCl_2CF_3$, $CHClFCF_3$, $CHF_2CF_3$, $CClF=CF_2$ |
| $CClF=CF_2$ | $CHClFCF_3$, $CHF_2CF_3$ |
| $CF_2=CF_2$ | $CHF_2CF_3$ |
| $CHCl=CCl_2$ | $CH_2ClCCl_2F$, $CH_2ClCClF_2$, $CH_2ClCF_3$, $CH_2FCF_3$ |
| $CCl_3CCl=CCl_2$ | $CCl_3CHClCCl_2F$, $CCl_2FCHClCCl_2F$, $CClF_2CHClCCl_2$, $CClF_2CHClCClF_2$, $CClF_2CHClCF_3$, $CF_3CHClCF_3$ |
| $CCl_3CF=CCl_2$ | $CCl_3CF_2CHCl_2$, $CCl_2FCF_2CHCl_2$, $CClF_2CF_2CHCl_2$, $CF_3CF_2CHCl_2$ |
| $CClF_2CCl=CCl_2$ | $CClF_2CClFCHCl_2$, $CF_3CClFCHCl_2$, $CF_3CClFCHClF$ |
| $CCl_2FCF=CCl_2$ | $CCl_2FCF_2CHCl_2$, $CClF_2CF_2CHCl_2$, $CF_3CF_2CHCl_2$ |
| $CF_3CF=CCl_2$ | $CF_3CF_2CHCl_2$ |
| $CClF_2CF=CClF$ | $CClF_2CF_2CHClF$, $CF_3CF_2CHClF$ |
| $CCl_3CF=CF_2$ | $CCl_3CF_2CHF_2$, $CCl_2FCF_2CHF_2$, $CClF_2CF_2CHF_2$, $CF_3CF_2CHF_2$ |
| $CClF=CClF$ | $CHClFCClF_2$, $CHF_2CClF_2$ |
| $CHCl=CHCl$ | $CHClFCH_2Cl$, $CHF_2CH_2Cl$, $CHF_2CH_2F$ |

The haloolefin can be delivered neat or as a component of a product stream containing nonolefinic components. For example, the haloolefin, to be fluorinated by addition of HF with the production of a saturated material, can be an impurity in a fluorinated product stream such as $CHCl=CF_2$ in $CF_3CH_2F$ as disclosed in U.S. Pat. No. 4,158,675 to Porter.

Representative fluorinated haloolefins that carry at least one more fluorine substituent than the haloolefin reactant of the process of the invention include:

$CCl_2=CClF$, $CClF=CHF$, $CClF=CHCl$
$CHCl=CClF$, $CHF=CCl_2$, $CHCl=CF_2$,
$CHF=CHCl$ and
$CHF=CHF$, $CH_2=CClF$, $CHF=CF_2$, $CCl_2=CF_2$
and
$CClF=CF_2$.

The process is conveniently conducted batchwise by mixing the reactants in a closed or ventible system and heating the mixture under agitation at a desired temperature and pressure, the pressure being controlled with a pressure-relief valve. The process can also be conducted continuously or semi-continuously with the haloolefin fed, with or without HF, to the reactor containing the alkali metal acid fluoride continuously or intermittently, and with the organic reaction product taken off continuously or intermittently. Since the organic reaction products are gaseous over the operating temperatures and pressures, it is convenient to bleed off a portion of the vapor phase intermittently or continuously during the course of the reaction.

The volatile reaction product mixture exiting the reactor contains the desired hydrogen-containing fluorinated saturated hydrocarbon(s), fluorinated unsaturated hydrocarbon(s), if any, and unreacted starting material, if any. The product mixture can be resolved into its components by any of a variety of well-known techniques. Unreacted haloolefin, unsaturated fluorinated material, even fluorinated saturated material still containing replaceable halogen can be recycled to the reactor for further HF addition and/or halogen exchange fluorination reactions.

The reaction vessel is constructed of materials resistant to the action of the reactants. Examples of such materials include stainless steels, high nickel alloys such as "Hastelloy" and "Inconel", and plastics such as polyethylene, polychlorotrifluoroethylene, and polytetrafluoroethylene.

The fluorination and alkali metal acid fluoride regeneration temperatures can vary widely provided that they are sufficiently high to maintain the acid fluoride composition in a substantially molten condition, but not so high as to result in decomposition of the haloolefin reactant or the fluorination (HF addition and halogen exchange) products. The reaction temperatures will normally be within a range of from about 25° to 400° C., depending upon the particular haloolefin reactant, the fluorinated products and the melting characteristics of the alkali metal acid fluoride-based composition. Preferably the temperature will be within the 75° to 350° C. range, more preferably within the 150° to 325° C. range.

Reaction pressure is not critical. It may vary from subatmospheric to superatmospheric, but preferably the pressure is at least atmospheric. Superatmospheric pressures, up to about 30 atmospheres, may be preferred to the extent that the solubility of the haloolefin in the molten acid fluoride increases with increased pressure and results in increased reaction rate and/or conversion to the fluorocarbon product.

Reaction time may also vary widely depending on the nature of the haloolefin, the alkali metal acid fluoride and the result desired.

In the following examples, the product mixtures were analyzed by gas chromatography (GC) and mass spectroscopy (MS). The reactor employed was equipped with an agitator, temperature controller and a back-pressure regulator to enable control of the reaction pressure and to allow sampling of the organic reaction products during the course of the reaction.

EXAMPLE 1

To a Hastelloy C Parr autoclave (600 cc) was added 607.6 gm (4.0 mole) CsF and 82.9 gm (0.5 mole) tetrachloroethene. The autoclave was sealed, cooled to −78° C., and evacuated to ca. 100 torr. Then 100 gm (5.5 mole) HF was added. The reactor was allowed to warm to room temperature and then heated to 300° C. Time, temperature and pressure were monitored. The back pressure regulator was initially set to 300 psig to contain the reactor contents until a process pressure at 250° C. was determined. The back pressure was then decreased to allow sample collection. Samples were taken at T=1.75, 1.82, 2.4, 4.5, 22.4, 24.1, 24.5, and 28.0 hours. Total run time was 28 hours. Mass balance was 70%. Conversion of tetrachloroethene was 46%. Products, with selectivity in parenthesis, were as follows: $CF_3CHCl_2$ (51%), $CF_3CHClF$ (12%) and $CF_3CHF_2$ (6%). Other products formed in small amounts were: $CF_3CH_2Cl$, $CF_3CH_2F$, $CF_3CH_3$, $CClF_2CCl_2F$, $CCl_2=CClF$ and $CCl_2=CHCl$.

EXAMPLE 2

This example was carried out under essentially the same conditions as Example 1 except that the temperature was maintained at 250° C. The process yielded the same saturated products except for $CClF_2CCl_2F$, and $CClF=CHF$, $CClF=CHCl$ in addition to $CCl_2=CClF$. $CCl_2=CHCl$ was not observed.

EXAMPLE 3

To a "Hastelloy" C Parr autoclave (600 cc) was added 760 gm (5.0 mole) CsF and 109 gm (5.45 mole) HF. The autoclave was sealed and heated to 178° C. Then 131.3 gm (1.0 mole) trichloroethene was added. Samples were taken at T=2, 4, 6, 23, 25, 27, 29, 46.8 and 54 hours by venting the reactor into a cooled caustic solution and separating the lower phase which was then analyzed by GC or GC/MS. For each liquid sample, gas samples were also taken. Total run time was 75 hours.

The liquid samples consisted primarily of unreacted trichloroethene. The gas samples contained significant amounts of $CF_3CH_2Cl$, $CF_3CH_2F$, $CHCl=CClF$, $CHF=CCl_2$ and $CHCl=CF_2$. Trace amounts of $CHF_2CHF_2$ and dichloromethylene (2110) were also detected.

EXAMPLE 4

To a "Hastalloy" C shaker tube (100 cc) was added 4.0 gms (0.069 mole) KF. The shaker tube was sealed, cooled in dry ice and evacuated. Then 44.8 gms (0.390 mole) $CFC=CCl_2$ (HCFC-1121a) was distilled into the shaker tube followed by 29.5 gms (1.475 mole) HF. The tube was then warmed to 144°-160° C. and shaken for 16 hours. After cooling to 0° C., the tube contents were neutralized by pouring into 27% aqueous $K_2HPO_4$ and separating the organic phase with a separatory funnel. Conversion of $CFH=CCl_2$ was 32.5% with 96% selectivity to the HF addition product $CH_2F-CFCl_2$ (HCFC-132c).

What is claimed:

1. A process for the fluorination of a haloolefin having at least one halogen selected from the group consisting of chlorine and fluorine attached to an unsaturated carbon atom to a saturated fluorinated addition produce having at least one more fluorine in the molecule than said haloolefin which comprises the following steps: (1) contacting the haloolefin with an anhydrous substantially molten composition containing an alkali metal acid fluoride, at a temperature below the decomposition temperature of said haloolefin or said fluorinated product, whichever is lower, to form a reaction mixture; (2) agitating said mixture at said temperature and at a pressure and for a time sufficient to yield at least one saturated fluorinated addition product having at least one more fluorine in the molecule than said haloolefin; and (3) isolating and recovering said fluorinated product.

2. A process as in claim 1 wherein said haloolefin starting material is selected from the group consisting of $CCl_2=CCl_2$, $CHCl=CCl_2$ and $CFH=CCl_2$.

3. A process as in claim 1 wherein said saturated fluorinated product is selected from the group consisting of 1,1,1-trifluorochloroethane, 1,1,1,2-tetrafluoroethane, 2,2-dichloro1,1,-trifluoroethane, 1,1,1,2-tetrafluoro-2-chloroethane, pentafluoroethane, and $CH_2F-CFCl_2$.

4. A process as in claim 1 wherein said alkali metal is selected from the group consisting of Cs, Rb and K.

5. A process as in claim 1 wherein said temperature is about 150° C. to about 325° C.

6. A process as in claim 1 wherein said pressure is about atmospheric pressure to about 30 atmospheres.

* * * * *

UNITED STATES PATENT AND TRADEMARK OFFICE
CERTIFICATE OF CORRECTION

PATENT NO.  : 5,045,634

DATED       : September 3, 1991

INVENTOR(S) : Richard Edward Fernandez, et al

It is certified that error appears in the above-identified patent and that said Letters Patent is hereby corrected as shown below:

Col. 8, line 56, "produce" should read --product--.

Signed and Sealed this

Eighteenth Day of May, 1993

Attest:

MICHAEL K. KIRK

Attesting Officer

Acting Commissioner of Patents and Trademarks